(12) United States Patent
Ullman

(10) Patent No.: US 6,265,220 B1
(45) Date of Patent: Jul. 24, 2001

(54) ASSAY FOR HOMOCYSTEINE

(76) Inventor: Edwin F. Ullman, 135 Selby La., Atherton, CA (US) 94027

( * ) Notice: Subject to any disclaimer, the term of this patent is extended or adjusted under 35 U.S.C. 154(b) by 0 days.

(21) Appl. No.: 09/340,275

(22) Filed: Jun. 25, 1999

Related U.S. Application Data

(60) Provisional application No. 60/090,992, filed on Jun. 29, 1998.

(51) Int. Cl.$^7$ .................................................. G01N 33/48
(52) U.S. Cl. ........................... 436/86; 436/164; 436/166; 436/63; 436/92; 436/96; 436/808; 422/61
(58) Field of Search ..................................... 436/164, 166, 436/92, 96, 63, 86, 808, 810, 811; 422/61

(56) References Cited

U.S. PATENT DOCUMENTS

| | | |
|---|---|---|
| 4,940,658 | 7/1990 | Allen et al. . |
| 4,952,336 | 8/1990 | Byrnes et al. . |
| 4,978,632 | 12/1990 | Mach et al. . |
| 5,478,729 | 12/1995 | Van Atta et al. . |

FOREIGN PATENT DOCUMENTS

WO 93/15220   8/1993   (WO) .

OTHER PUBLICATIONS

Alvarez–Coque, et al; *Spechtrochim.Acta. Part A*; 44A(12): 1461–4; (1988); Some Observations on the Reaction of Cysteine with o–phthalaldehyde.

Ueland, et al., *Clin. Chem.*; 39(9): 1764–1779; (1993); Total Homocysteine in Plasma or Serum: Methods and Clinical Applications.

Andersson, et al., *Clin. Chem.*; 39(8): 1590–1597; (1993); Homocysteine and Other Thiols Determined in Plasma by HPLC and Thiol–Specific Postcolumn Derivatization.

Fiskerstrand, et al., *Clin. Chem.*; 39(2): 236–271; (1993); Homocysteine and Other Thiols in Plasma and Urine: Automated Determination and Sample Stability.

Refsum, et al., *Clin. Chem.*; 31(4): 624–628; (1985); Radioenzymic Determination of Homocysteine in Plasma and Urine.

Jue, et al., *Analytical Biochemistry*; 210: 39–44; (1993); Identification of Cysteine Residues Alkylated with 3–Bromopropylamine by Protein Sequence Analysis.

Chen, et al., *Biochim. Biophy. Acta*; 576(2): 440–455; (1979); Fluorescence Properties of o–phthalaldehyde Derivatives of Amino Acids.

Lee, et al., *J. Biol. Chem.*; 254: 6248; (1979); Derivatization of Cysteine and Cystine for Flourescence Amino Acid Analysis with the o–phthaldialdehyde/2–Mercaptoethanol Reagent.

Metz, et al., *J. Chromatogr.*; 330(2): 307–313; (1995); Off–line Liquid Chromatographic–Mass Spectrometric Studies of Fluorescent βaminothiol–o–phthalaldehyde Derivatives.

Puri, et al., *Anal. Biochem.*; 173(1): 26–32; (1988); Reaction of Low Molecular Weight Aminothiols with o–phthalaldehyde.

Simons, Jr., et al., *J. Chem. Soc. Chem Comm.*; 11: 374–375; (1977); Preparation of a Stable, Fluorescent 1–Alkylthio–2–alkylisoindole.

Simpson, et al., *J. Chromatogr.*; 261(3); 407–414; (1983); Off–line Liquid Chromatographic–Mass Spectrometric Studies of o–phthaladehyde–Primary Amine Derivatives.

Simons, Jr., et al., *J. Org. Chem.*; 46(23): 4739–4744; (1981); Structure and Properties of a Stable Isoindole. The Dimethyl Acetylenedicarboxylate–1–(Ethylthio)–2–η–propylisoindole Substitution Product.

Simons, Jr., et al., *J. Am. Chem. Soc.*; 98(22): 7098–7099; (1976); The Structure of the Fluorescent Adduct Formed in the Reaction of o–phthalaldehyde and Thiols with Amines.

Simons, Jr., et al., *Anal. Biochem.*; 90(2): 705–725; (1978); Reaction of o–phthalaldehyde and Thiols with Primary Amines: Fluorescence Properties of 1–Alkyl(and aryl)thio–2–Alkylisoindoles.

Simons, Jr., et al., *J. Org. Chem.*; 43 (14): 2886–1291; (1978); Reaction of o–phthalaldehyde and Thiols with Primary Amines: Formation of 1–Alkyl(and aryl)thio–2–Alkylisoindoles.

*Primary Examiner*—Lyle A. Alexander
(74) *Attorney, Agent, or Firm*—Hana Verny

(57) ABSTRACT

A non-immunochemical method is disclosed for determining homocysteine in a sample. A combination of the sample and a first compound that comprises a cis-1,4-dioxo-2-butene moiety or hydrolytically derived precursor thereto is provided in a liquid medium. The combination is subjected to conditions under which homocysteine reacts with the cis-1,4-dioxo-2-butene moiety or hydrolytically derived precursor thereto to form a product, which is then detected without separation of the product from the medium. A second compound such as a mercaptan containing reagent or an antibody for cysteine can optionally be included to facilitate discrimination of the product formed from homocysteine from products formed from other amines in the sample. The product from the reaction of homocysteine has a six-member ring fused to an unsaturated five-member ring. The junction of the rings is comprised of the nitrogen of homocysteine and an atom that comprises a double bond. The six-member ring comprises the sulfur atom of homocysteine. The amount of the product detected is related to the amount of homocysteine in the sample.

20 Claims, No Drawings

ASSAY FOR HOMOCYSTEINE

This application claims benefit of Provisional Appln 60/090,992 filed Jun. 29, 1998.

BACKGROUND OF THE INVENTION

1. Field of the Invention

This invention relates generally to the area of assays and in particular to the determination of homocysteine.

Homocysteine (Hcy) is one in a series of intermediates produced along the transsulfuration pathway in which methionine is eventually converted to cysteine (Cys). The exclusive source of Hcy in mammals derives from the product of the enzyme-catalyzed hydrolysis of S-adenosylhomocysteine. Once formed, Hcy may reenter the cycle through remethylation and conversion to methionine or combine with serine to form cystathionine, which is ultimately converted to Cys. The major metabolic pathway for the methylation of Hcy by methionine synthase requires vitamin $B_{12}$ (cobalamine) as a methyl-transfer cofactor and 5-methyl-tetrahydrofolate as the ultimate methyl source.

Hcy and Cys are sulfhydryl amino acids that are homologs. Hcy is $HOOCCH(NH_2)CH_2CH_2SH$ and Cys is $HOOCCH(NH_2)CH_2SH$. Hcy and Cys are immunologically related because an antibody generated against Hcy would be expected to crossreact with Cys. This is so because there is only a single carbon difference between the two compounds in the length of their amino acid side chains. Because of this immunological relationship between Hcy and Cys, it is difficult to develop an assay that can distinguish between Hcy and Cys by immunological methods.

Elevated levels of serum Hcy have been associated with insufficient intake of vitamin $B_{12}$ or folate, or a deficiency in the ability to properly utilize these two vitamins. Moderately elevated levels of Hcy usually can be brought into balance by administering folate, a treatment for which there are few adverse side effects.

Both individuals who are anemic and those who are heterozygous for a defective cystathionine synthase gene are particularly susceptible to elevated Hcy levels following methionine loading. Genetic predisposition is the most common cause of moderate homocysteinuria (build-up of Hcy in urine) in otherwise healthy patients. Lastly, there appears to be a correlation between moderately elevated levels of Hcy and cardiovascular disease. For these reasons, there has been great interest in developing an accurate Hcy assay.

Several immunochemical methods for the assay of homocysteine have been described. The fundamental problem is that cysteine and homocysteine differ by only one methylene group and it is difficult to prepare antibodies that discriminate sufficiently without derivitization of one or both of the compounds. These steps add to the complexity of the method. Additionally, an immunochemical method requires that the assay be carried out on an immunochemical analyzer. Since an assay for homocysteine would be of use as a general screen in much the same way as an assay for cholesterol, HDL and LDL, it would be highly desirable to be able to run a homocysteine assay on the same instruments as the cholesterol, HDL and LDL assays.

There are several techniques to quantitate total homocysteine (Hcy) as well as distinguish between the reduced form and oxidized forms containing a disulfide, which may be free or protein-bound (primarily to albumin).

An excellent overview of the causes of homocysteinuria as well as an update on the current methods of clinical analysis can be found in Ueland, et al., *Clin. Chem.* 39(9):1764–1779 (1993).

An enzymatic method for a Hcy assay is described by Sundrehagen, et al., PCT/GB93/00138, where Hcy is assayed indirectly by measuring the product concentration following the enzyme catalyzed conversion of Hcy to S-adenosyl homocysteine.

High performance liquid chromatographic (HPLC) methods for Hcy and Cys are known in the art. This analytical method discriminates between Hcy and Cys by differential adsorption and elution of the compounds on a chromatographic support. Andersson, et al., Clin. Chem. 39(8):1590–1597 (1993) describe the determination of total, free and reduced Hcy and Cys.

Hcy and Cys analysis by means of a gas chromatograph-mass spectrometer is described in Allen, et al., U.S. Pat. No. 4,940,658. Allen, et al., PCT/US92/05727 describe a chromatographic assay for cystathionine, the intermediary amino acid between Hcy and Cys produced in the metabolism of methionine.

Fiskerstrand, et al., *Clin. Chem.* 39(2):263–271 (1993) describe a fully automated analysis of total Hcy involving fluorescent labeling of serum thiols, followed by chromatographic separation of the Hcy derivative from the other sulfur-containing compounds.

Identification of Hcy by HPLC methods often involves derivatization with fluorescent reagents such as is described in Fiskerstrand, supra, or a radioenzymatic technique such as is described in Refsum, et al., *Clin. Chem.* 31(4) 624–628 (1985). In addition, identification of Cys by protein sequence analysis involves derivatization with alkylating reagents. See, for example, Jue, et al., *Analytical Biochemistry* 210:39–44 (1993).

Unfortunately, chromatographic methods have the disadvantage of being slow and labor intensive. Furthermore, current methods of Hcy analysis require prior derivatization with fluorescent labels, such as bromobimane, in which the bromomethyl group reacts with the free thiol of Hcy, thus forming a thioether and releasing free bromide ion. The bromobimane reagent also reacts with all other free thiols in solution; therefore, chromatographic separation of the various derivatized sulfur-containing species is necessary.

There are numerous techniques for handling undesirable cross-reactants. Brynes, et al. (U.S. Pat. No. 4,952,336), describe a method of pretreating a sample with an aqueous periodate solution to eliminate cross-reactants in an amphetamine-methamphetamine immunoassay. Stevenson, PCT/GB90/01649, pertains to an improved immunoassay where the level of interference from rheumatoid factor is reduced by pretreating the sample with a reducing agent. U.S. Pat. No. 4,978,632 (Mach, et al.) pertains to an improved immunoassay where the level of interference from blood and blood products is eliminated by pretreating the sample with an oxidizing agent. These pretreatment methods only affect the cross-reactants; none of the methods affect the analyte.

As many of the current methods of Hcy analysis rely on cumbersome chromatographic techniques, there is a need for a faster and simpler assay for Hcy.

2. Description of the Related Art

U.S. Pat. No. 5,478,729 (Van Atta, et al.) discloses an immunoassay for homocysteine.

Simons, et al., (Simons 1) *J. Am. Chem. Soc.,* (1976) 98(22), 7098–7099, disclose the reaction of amino acids with o-phthalaldehyde and thiols to form fluorescent products.

Simons, et al., (Simons 2), *Anal. Biochem.* (1978) 90(2), 705–725, disclose the fluorescent properties of 1-alkyl (and aryl) thio-2-alkylisoindoles formed by the reaction of o-phthalaldehyde and thiols with primary amines.

Simons, et al., (Simons 3), *J. Org. Chem.* (1978) 43(14), 2886–91, disclose the formation of 1-alkylthio-2-alkylisoindoles from o-phthalaldehyde, mercaptols and amino acids.

Alvarez-Coque, et al., *Spectrochim. Acta, Part A* (1988) 44A(12), 1461–4, disclose the reaction of cysteine with o-phthalaldehyde to produce a fluorescent compound at elevated temperatures but not at room temperature.

Chen, et al., *Biochim. Biophys. Acta* (1979) 576(2), 440–55, disclose the fluorescence quantum yields of the product of o-phthalaldehyde, amino acids and thiol compounds and show that cysteine reacts to give an unstable, weakly fluorescent product unless its sulfhydryl group is blocked.

Lee, et al., *J. Biol. Chem.,* (1979) 254, 6248, disclose the modification of the cysteine mercapto group to facilitate formation of a highly fluorescent product upon reaction with o-phthalaldehyde.

Metz, et al., *J. Chromatogr.* (1985) 330(2) 307–13, disclose the post-column derivatization of cysteine and other α-aminothiols with phthalaldehyde and determination of the structures of the fluorescent products.

Puri, et. al., *Anal. Bioochem.* (1988) 173(1), 26–32, disclose monitoring of the reaction of glutathione, homocysteine and cysteine with o-phthalaldehyde by measuring the fluorescence of the isoindole derivatives that are formed to compute molar transition energies.

Simons (Simon 4) , *J. Chem Soc., Chem Comm.,* (1977) 11, 374, disclose the formation of 1-t-butylthio-2-propylisoindole from o-phthalaldehyde, t-butylthiol and propylamine.

Simpson, et al., (Simpson 1) *J. Chromatogr.* (1983) 261 (3), 407–14, disclose off-line liquid chromatographic-mass spectrometric studies showing that the structure of the fluorescent products of the reaction of o-phthalaldehyde, primary amines and thiols are 1-alkylthio-2-alkyl-substituted isoindoles.

Simons, et al., (Simons 5) *J. Org. Chem.* (1981) 46(23), 4739–4744, disclose the formation of dark red substituted isoindoles upon reaction of dimethyl acetylenedicarboxylate with 1-alkylthio-2-propylisoindoles.

SUMMARY OF THE INVENTION

One aspect of the present invention is a non-immunochemical method for determining homocysteine in a sample containing homocysteine and other amines. A combination of the sample and a first compound that comprises a cis-1,4-dioxo-2-butene moiety, or a hydrolytically derived precursor thereto, is provided in a liquid medium. The combination is subjected to conditions under which homocysteine reacts with the cis-1,4-dioxo-2-butene moiety or hydrolytically derived precursor thereto to form a product, which is then detected without separation of the product from the medium.

The cis-1,4-dioxo-2-butene moiety of the first compound usually has the structure:'

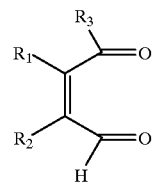

wherein $R^1$, $R^2$ and $R_3$ are independently hydrogen, alkyl, aryl, aralkyl, or alkylene, wherein one or more hydrogens of the above may each be substituted with a substituent and wherein $R^1$ and $R^3$ and/or $R^2$ may be taken together to form a 5 to 7 member ring, which contains one or more double bonds.

Another aspect of the present invention is a method for determining the amount of homocysteine in a sample. The sample is provided in combination with one or more reagents that cause the formation of a product, which has a six-member ring fused to an unsaturated five-member ring. The junction of the rings is comprised of the nitrogen of homocysteine and an atom that comprises a double bond. The six-member ring comprises the sulfur atom of homocysteine. The amount of the product is then detected and is related to the amount of homocysteine in the sample.

Another embodiment of the present invention is a method for determining homocysteine in a sample that also contains other amines. The sample is combined with a first compound that comprises a cis-1,4-dioxo-2-butene moiety or hydrolytically derived precursor thereto in the presence of a reagent comprised of a sulfhydryl group and a signal deactivator. The signal deactivator provides means for inhibiting signal from reaction products into which it is incorporated or with which it can bind or react. The amount of signal from any reaction product that does not contain or is not bound to the signal deactivator is measured to determine the amount of homocysteine in the sample.

Another embodiment of the present invention is directed to kits, which can comprise in packaged combination (a) a compound that comprises a cis-1,4-dioxo-2-butene moiety or hydrolytically derived precursor thereto and (b) other reagents for conducting a method for determining the amount of Hcy in a sample.

DETAILED DESCRIPTION OF THE INVENTION

The present invention is directed to a non-immunochemical method for the quantitative determination of homocysteine that is adaptable for use on instrumentation commonly available in the clinical laboratory or for point of care use. As such, the present invention avoids immunological methods. The present invention has particular applicability for clinical instruments since the present method merely requires the mixing of the sample with the reagents of the invention followed by a reading step. No separation step is required, which is important in the area of clinical instruments because these instruments have no provision for carrying out a separation. To provide a clinically useful assay, the present invention utilizes differences in behavior of Cys and Hcy toward reaction with a compound that comprises a cis-1,4-dioxo-2-butene moiety or hydrolytically derived precursor thereto.

As mentioned above, one embodiment of the present invention is a non-immunochemical method for determining homocysteine in a sample. A combination is formed comprising the sample and a first compound that comprises a cis-1,4-dioxo-2-butene moiety, or hydrolytically derived precursor thereto. The sample is usually any solution, synthetic or natural, suspected of containing homocysteine, which usually will also contain other amines such as other aminoacids. Such solution may be, or may include, a body fluid such as, for example, whole blood, blood fractions such as serum and plasma, urine and the like. The amount of the sample depends on the nature of the sample. For fluid samples such as whole blood, saliva, urine and the like the amount of the sample is usually about 1 to 1000 microliters, more usually, about 10 to 100 microliters although instruments employing microfluids that are currently under development may permit sample sizes as low as 1 nanoliter. The sample can be pretreated and can be prepared in any convenient medium, which does not interfere with the reactions conducted as part of the present methods.

It may be desirable to determine either the free or total Hcy in the sample. When total Hcy is to be determined it will be necessary to provide a means to reduce any Hcy that exists as a disulfide during or prior to the assay in accordance with the present invention. Although dithiols such as dithioerythreitol are frequently used to reduce disulfides, reducing agents that do not have thiol groups are preferred because of the tendency of excess thiols to interfere with the present method. Tertiary phosphines, such as triscarboxyethylphosphine, are particularly preferred since they are relatively stable and cause rapid and complete reduction of disulfides. However, other reducing agents can be used including borohydrides, such as sodium borohydride. Alternatively, phosphorothioates or NADH with an enzyme catalyst such as cystine reductase can be used. Reagents useful for reduction of disulfides are well known in the art and have been reviewed by Jocelyn, Peter C. in *Methods Enzymol.* (1987), 143 246–56. In one approach an amount of triscarboxyethylphosphine in excess of that required to reduce the maximum number of sulfhydryl groups likely to be present in the sample may be added to the sample in a suitable medium.

The first compound comprises a cis-1,4-dioxo-2-butene moiety or hydrolytically derived precursor thereto, wherein the cis-1,4-dioxo-2-butene moiety usually has the structure:

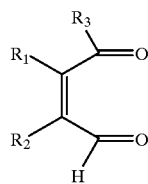

wherein $R^1$, $R^2$ and $R^3$ are independently hydrogen, alkyl, aryl, aralkyl, or alkenyl, wherein one or more hydrogens of the above may each be substituted with a substituent and wherein $R^1$ and $R^3$ and/or $R^2$ may be taken together to form a 5 to 7 member ring, which contains one or more double bonds.

"Hydrolytically derived precursor to a cis-1,4-dioxo-2-butene moiety" means a compound which upon exposure to water at a pH of 2 to 11 for periods of up to an hour reacts with the water to form a cis-1,4-dioxo-2-butene moiety. Such compounds include by way of example and not limitation 1,4-dioxo-2-butenes in which one or both of the oxygens of the carbonyl groups is replaced by two halogen atoms other than fluorine, by one halogen and one alkoxy or siloxy group, by two alkoxy or siloxy groups, by an arylimino group, and the like. Although such a precursor will be converted to a cis-1,4-dioxo-2-butene moiety under the above conditions, it is not necessary that the precursor actually be converted to a cis-1,4-dioxo-2-butene moiety during reaction with homocysteine by the method of this invention so long as homocysteine can react with it to form the products described below.

"Alkyl" means a branched or unbranched saturated monovalent hydrocarbon radical containing at least 1 carbon atom, usually 1 to 30 carbon atoms, such as methyl, ethyl, propyl, tert-butyl, n-hexyl, n-octyl and the like.

"Lower alkyl" means a branched or unbranched saturated monovalent hydrocarbon radical containing 1 to 6 carbon atoms, such as methyl, ethyl, propyl, isopropyl, tert-butyl, butyl, n-pentyl and the like, unless otherwise indicated.

"Cycloalkyl" means a saturated monovalent monocyclic hydrocarbon radical containing 3–8 carbon atoms, such as cyclopropyl, cyclobutyl, cyclopentyl, cyclohexyl, cycloheptyl and cyclooctyl.

"Alkenyl" means a branched or unbranched unsaturated hydrocarbon radical containing at least one ethenylic bond and at least 2 carbon atoms, usually 2 to 30 carbon atoms, such as ethenyl, propenyl, n-butenyl, isopropenyl, isobutenyl, n-pentenyl, isopentenyl and the like, unless otherwise indicated.

"Lower alkenyl" means a branched or unbranched unsaturated divalent hydrocarbon radical containing at least one ethenylic bond and 2 to 6 carbon atoms, such as ethenylene, propenylene, 2-methylpropenylene, 1,2-dimethylpropenylene, pentenylene, and the like.

"Aryl" means an organic radical derived from an aromatic hydrocarbon or aromatic heterocycle by the removal of one atom, e.g., phenyl from benzene, naphthyl from naphthalene, pyrryl form pyrrole, pyridyl for pyridine, thienyl from theophene, phenanthryl from phenanthrene, oxazyl from oxazole, and the like.

"Aralkyl" means an alkyl substituted with aryl such as, e.g., phenylethyl, pyridylbutyl, etc.

"Substituted" means that a hydrogen atom of a molecule has been replaced by another atom, which may be a single atom such as a halogen, etc., or part of a group of atoms forming a functionality such as a substituent having from 1 to 50 atoms (other than the requisite hydrogen atoms necessary to satisfy the valencies of such atoms), which atoms are independently selected from the group consisting of carbon, oxygen, nitrogen, sulfur, halogen (chlorine, bromine, iodine, fluorine) and phosphorus, and which may or may not be bound to one or more metal atoms.

"A substituent having from 1 to 50 atoms (other than the requisite hydrogen atoms necessary to satisfy the valencies of such atoms), which atoms are independently selected from the group consisting of carbon, oxygen, nitrogen, sulfur, halogen and phosphorus" means an organic radical. Usually, the organic radical has 1 to 50 atoms other than the requisite number of hydrogen atoms necessary to satisfy the valencies of the atoms in the radical. Generally, the predominant atom is carbon (C) but may also be oxygen (O), nitrogen (N), sulfur (S), phosphorus (P), wherein the O, N, S, or P, if present, are bound to carbon or one or more of each other or to hydrogen or a metal atom to form various functional groups, such as, for example, carboxyl groups (carboxylic acids), hydroxyl groups (alcohols), mercapto groups (thiols), carboxamides, carbamates, carboxylic acid esters, sulfonic acids, sulfonic acid esters, phosphoric acids, phosphoric acid esters, ureas, carbamates, phosphoramides, sulfonamides, ethers, sulfides, thioethers, olefins, acetylenes, amines, ketones, aldehydes and nitriles, and alkyl, alkylidine, aryl, aralkyl, and alkyl, aryl, and alkaryl substituted with one or more of the aforementioned functional groups.

Exemplary of first compounds that may be employed in the present invention, by way of illustration and not limitation, are cis-1,4-dioxo-2-butene moieties such as, 3-(2-furoyl)-quinoline-2-carboxaldehyde, naphthalene 2,3-dialdehyde, o-phthalaldehyde, naphthoquinone-5-carboxaldehyde, quinoline 2,3-dicarboxaldehyde, 3-trifluoroacetylpyridine-4-carboxaldehyde and hydrolytically derived precursors to each of the last four of the above compounds, respectively, such as 2,7-dimethoxy-2,7-dihydroisobenzofuran, 5-(bis-methoxymethyl)-naphthoquinone, 3-(dibromomethyl)-2-quinaldehyde, and the 0-tosyloxime of 3-trifluoroacetylpyridine-4-carboxaldehyde and so forth.

In addition to the first compound mentioned above, other reagents may be employed in the present method. Such reagents include any reagents that facilitate the formation of a product of the reaction with Hcy that has a six-membered ring fused to an unsaturated five-membered ring wherein the junction of the rings is comprised of the nitrogen of homocysteine and an atom that comprises a double bond and wherein the six-membered ring comprises the sulfur atom of homocysteine. The product comprises the following general structure wherein Z may be hydrogen or may taken separately as different substituents or taken together to form one or more rings or multiple bonds:

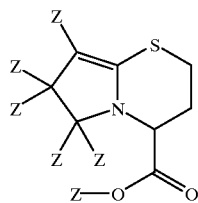

It should be noted that the underlying principle of the present invention, as explained above, is that Hcy reacts with the first compound to form adducts or products that may provide a signal that is distinguishable from the signal corresponding to the product, if any, that is produced with Cys and other amines, as discussed more fully hereinbelow. Accordingly, the first compound may be designed so that the products of the reaction may be distinguishable because of different spectral properties such as a difference in wavelength or intensity of fluorescence or because the product of the first compound and Cys is not formed to any appreciable extent or is not fluorescent to any appreciable extent.

Where there is only minimal difference between the products formed from Hcy and Cys, additional reagents may be used in the present method. For example, a second compound may be employed in the liquid medium to facilitate discrimination of the product formed from homocysteine from products formed from other amines such as cysteine in the sample. The second compound may be an antibody for the cysteine reaction product, which binds to the cysteine product, or a compound that comprises a mercaptan, which reacts with the cysteine product. Mercaptan-containing reagents include specific binding pair members comprised of a ligand-mercaptan conjugate and an anti-ligand receptor; particles having antiligand receptors, antibodies, or mercaptans on their surface, particularly light absorbing particles; conjugates of mercaptans and other signal deactivators such as fluorescence quenchers; and the like. The second compound is employed in an amount sufficient to reduce the effect of Cys or other amines to a level that permits discrimination of Hcy products from other products. Generally, this amount will be an excess over the highest expected amount of Cys or other amines. Exemplary protocols in which additional reagents are employed are discussed in more detail hereinbelow.

The combination is subjected to conditions under which homocysteine reacts with the cis-1,4-dioxo-2-butene moiety or hydrolytically derived precursor thereto to form the aforementioned product. Preferably, the medium for carrying out the methods in accordance with the present invention is an aqueous medium. Other polar cosolvents may also be employed in the medium, usually oxygenated organic solvents of from 1–6, more usually for 1–4 carbon atoms, including alcohols, ethers and the like. Usually, such cosolvents are present in less than about 70 weight percent, more usually, in less than about 30 weight percent. Additionally, various ancillary materials are frequently employed in the method in accordance with the present invention. For example, buffers are normally present in the assay medium, as well as stabilizers for the assay medium and the assay components; surfactants, particularly non-ionic surfactants; binding enhancers, e.g., polyalkylene glycols; or the like.

The pH for the medium is usually in the range of about 2 to about 11, preferably, about 4 to about 9. The pH is chosen so as to maximize the rate of the reaction of homocysteine with the first compound and to optimize the selectivity of the reaction of the first compound with homocysteine relative to it reaction with other amino acids. Various buffers may be used to achieve the desired pH and maintain the pH during the method. Illustrative buffers include borate, phosphate, carbonate, Tris, barbital, and the like. The particular buffer employed is not critical to the method but one buffer may be preferred over others in certain circumstances.

Moderate temperatures are normally employed for carrying out the method. The temperature may be constant or may vary. Usually, a constant temperature is employed during the reaction step. The temperature employed is usually about 10 to about 80° C., more usually, about 15 to about 45° C. It is within the purview of the present method to carry out the reaction with the first compound at an elevated temperature and perform the detection at a lower temperature such as, for example, ambient temperature. However, relatively lower temperatures are preferred for the reaction with the first compound so as to provide a protocol that it consistent with protocols used on commercial clinical chemistry analyzers.

The concentration of the Hcy to be determined generally varies from about $10^{-4}$ to about $10^{-8}$ M, usually, from about $10^{-5}$ to about $10^{-7}$ M. The amount of the first compound usually is determined by the rate of the reaction of Hcy with the first compound and is usually about $10^{-4}$ to $10^{-1}$ M, usually about $10^{-3}$ to $10^{-1}$ M. When a conjugate of a mercaptan and a signal deactivator is used as an additional reagent normally the highest concentration will be used that will not interfere with the reaction of homocysteine with the first compound. In many instances the final concentration of each of the reagents is determined empirically to optimize the sensitivity of the method over the range of interest for the suspected Hcy concentration.

The order of addition of the various reagents may be varied. Any pretreatment of the sample, for example to reduce homocysteine that may be present as a disulfide, is carried out prior to or simultaneously with the addition of the other reagents depending on the nature of the pretreatment. Usually, the sample is combined with a mixture of the first compound and other chemically reactive reagents. Specific binding substances such as antibodies, if used, will normally be added in a subsequent step. Depending on the nature of the reagents one or more incubation periods may be utilized ranging from about 5 seconds to 1 hours, usually from about 20 seconds to 10 minutes.

The time period for carrying out the present method with respect to the reaction of Hcy with the cis-1,4-dioxo-2-butene moiety or hydrolytically derived precursor thereto is from about 5 seconds to 1 hour, usually from about 20 seconds to 10 minutes, more usually, about 30 seconds to about 5 minutes.

Following the above reaction, the product formed is then detected without separation of the product from the medium by measurement of its fluorescence. For this purpose the reaction medium will usually be irradiated with light having wavelengths in the range 300 to 800 nm, more usually 400 to 700 nm, preferably 500 to 650 nm and the emitted light will have wavelengths ranging from 10 to 400 nm longer wavelength than the light used for irradiation, preferably 50 to 400 nm.

In the event that Cys or other amines reacts with the first compound under the reaction conditions employed in the present method, the product of the reaction with Cys is much less fluorescent and/or less stable than that formed from Hcy or may be rendered less fluorescent or less stable by the addition of additional reactants. Such amines include any of the naturally occurring aminoacids or amines associated with proteins and polypeptides, biogenic polyamines such as cadaverine and putricene, and the like. By inclusion of a conjugate of a non-fluorescent quencher and a mercaptan in the assay mixture, the conjugate will be incorporated into the product formed by reaction of Cys and other amines with the first compound but will not be incorporated into the product formed from Hcy. The resulting non-Hcy product(s) would be fluorescent if not for the introduction of the quencher, whereas the product produced by reaction of Hcy with the first compound which does not incorporate the conjugate will retain its fluorescence properties.

Alternatively, a conjugate of a ligand and a mercaptan can be used wherein the ligand is incorporated into the product (s) formed from the first compound and amines other than Hcy. These products can subsequently be rendered non-fluorescent by addition of a receptor capable of binding to the ligand and quenching the fluorescence. The ligand will normally be a small molecule of molecular weight under 2000 daltons for which a receptor is available. Preferably the ligand will be a hapten for which the corresponding antibody is available.

In another approach, the ligand can be a biotin derivative which can be bound by avidin or streptavidin, a cobalamine derivative which can be bound by intrinsic factor, a folate derivative which can be bound by folate binding protein, and the like. Where the receptor or antibody does not spontaneously cause quenching upon binding to the reaction product of amines other than Hcy and the first compound, the receptor or antibody can be conjugated to a quencher to effect quenching.

Alternatively, the receptor or antibody can be conjugated to a particle that can be moved out of the light path during the fluorescence measurement or that is itself a quencher by virtue of its ability to absorb the excitation and/or emitted light during the fluorescence measurement. In all of these methods in which a non-particulate quencher is used, the quencher can be a non-fluorescent dye that absorbs at the wavelength of fluorescence of the product(s) or a strong electron donor or acceptor that quenches fluorescence by causing an electron to be added or withdrawn from the excited state of the product(s). Such electroactive quenchers include quinones, polynitro compounds, azo compounds, aryl diamines, aminophenols, and the like.

In an alternate approach, the products(s) of other amines and the first compound can be discriminated from the product of reaction of Hcy by adding a chromogenic reagent, which produces a different color when it reacts with the Hcy product than with the product of other amines. For example, iso-indoles have been shown to react readily with acetylene-dicarboxylic acid derivatives, and the products, which are fumaryl-substituted iso-indoles, have intense long wavelength absorbance that will depend on the substitution pattern of the isoindole. Depending on their specific structures, these compounds may or may not be fluorescent but can by detected by their unique absorption spectrum. In general the fumaryl-substituted isoindoles absorb at wavelengths longer than 450 nm, and derivatives can be prepared that absorb at wavelengths as long as 700 nm where other components in the sample are relatively transparent.

The detection step is generally merely a step in which the signal is read. The signal is normally read using a fluorometer or in some instances an absorption spectrometer. As mentioned above, this is a significant advantage of the present method over known methods because no separation step is required and the method is easily adapted to clinical instruments. The signal detected in the method of the present invention is normally compared to that obtained using a standard or control having a known concentration of Hcy.

The following protocols for carrying out methods in accordance with the present invention are described next for purposes of illustration and should not be construed as limiting the scope of the invention. These protocols are merely examples of some of the particular protocols that may be employed. In each of the following concepts it is assumed, but not required, that any Hcy that exists as a disulfide will be reduced simultaneous with or prior to the planned reactions. Although the concepts are described in terms of detection by fluorescence, it is obvious that modulation of the electronic properties of products formed by the contemplated methods will permit other detection methods to be used such as, for example, electrochemical detection, light absorption and other methods that depend on the detection of electromagnetic radiation.

Before proceeding further with a description of these exemplary protocols in accordance with the present invention, a number of terms will be defined and described in detail.

Ligand—any organic compound for which a receptor naturally exists or can be prepared. Ligands of particular interest for this invention are relatively small molecules, usually greater than 100 and less than 2000 daltons although macromolecules including proteins, nucleic acids and polysaccharides may also be used. Illustrative ligands include haptens such as digoxin or dinitrophenyl and naturally occurring ligands such as biotin and folate. Ligands that may be used in this invention frequently have at least one sulfhydryl group that can be alkylated without preventing binding to the receptor and are sometimes referred to as conjugates of a mercaptan and a ligand.

Receptor ("antiligand")—any compound or composition capable of recognizing a particular spatial and polar organization of a ligand. Illustrative receptors include naturally occurring receptors, e.g., thyroxine binding globulin, antibodies, Fab fragments, lectins, nucleic acids, streptavidin, folate binding protein, and the like.

Antibody—an immunoglobulin that specifically binds to and is thereby defined as complementary with a particular spatial and polar organization of another molecule. The antibody can be monoclonal or polyclonal and can be prepared by techniques that are well known in the art such as immunization of a host and collection of sera (polyclonal), by preparing continuous hybrid cell lines and collecting the secreted protein (monoclonal) (see, e.g., Kohler and Milstein, *Nature* (1975) 265:495–497) or by cloning and expressing nucleotide sequences or mutagenized versions thereof coding at least for the amino acid sequences required for specific binding of natural antibodies. Antibodies may include a complete immunoglobulin or fragment thereof, which immunoglobulins include the various classes and isotypes, such as IgA, IgD, IgE, IgG1, IgG2a, IgG2b and IgG3, IgM, etc. Fragments thereof may include Fab, Fv and F(ab')$_2$, Fab', and the like. In addition, aggregates, polymers, and conjugates of immunoglobulins or their fragments can be used where appropriate so long as binding affinity for a particular molecule is maintained.

In general, in the preparation of a monoclonal antibody, an immunogen is injected into a mouse and, after a sufficient time, the mouse is sacrificed and spleen cells are obtained. The spleen cell chromosomes encoding desired immunoglobulins are immortalized by fusing the spleen cells with myeloma cells or with lymphoma cells, generally in the presence of polyethylene glycol. The resulting cells, which include the fused hybridomas, are allowed to grow in a selective medium, such as HAT-medium, and the surviving cells are grown in such medium using limiting dilution conditions. The cells are grown in a suitable container, e.g., microtiter wells, and the supernatant is screened for monoclonal antibodies having the desired specificity.

Various techniques exist for enhancing yields of monoclonal antibodies, such as injection of the hybridoma cells into a peritoneal cavity of a mammalian host, which accepts the cells, and harvesting the ascites fluid. Where an insufficient amount of the monoclonal antibody collects in the ascites fluid, the antibody is harvested from the blood of the host. Various conventional ways exist for isolation and purification of the monoclonal antibodies, so as to free the monoclonal antibodies from other proteins and other contaminants (see Kohler and Milstein, supra).

Particles—particles having an average diameter of at least about 20 nm and not more than about 100 microns, usually at least about 40 nm and less than about 20 microns, preferably, from about 0.10 to 2.0 microns average diameter, spherical or non-spherical, preferably spherical. The particles may have any density, but will preferably have of a density approximating water, generally from about 0.7 to about 1.5 g/ml. The particles may or may not have a charge; and, when they are charged, they are preferably negatively charged. They will frequently also be adsorptive or functionalizable so as to bind or attach at their surface, either directly or indirectly, a receptor or antibody or thiol groups.

The particles may be of any composition, frequently latex, carbon, metal sols, dye crystallites, dendrimers, silicates, metal oxides, and the like. Latex particles are preferred and comprise particulate water suspendable water insoluble polymeric material. Latex is frequently a substituted polyethylene such as polystyrene-butadiene, polyacrylamide, polystyrene, polystyrene with amino groups, poly-acrylic acid, polymethacrylic acid, acrylonitrile-butadiene, styrene copolymers, polyvinyl acetate-acrylate, polyvinyl pyridine, vinyl-chloride acrylate copolymers, polyvinyl chloride, polyvinylnaphthalene and the like. Non-crosslinked polymers of styrene and carboxylated styrene or styrene functionalized with other active groups such as amino, hydroxyl, halo and the like are particularly preferred. Frequently, copolymers of substituted styrenes with dienes such as butadiene will be used.

The particles can frequently function as a quencher of the fluorescence of the products of the first compound and amines other than homocysteine. Where the particles are intrinsically opaque as are dye crystallites, carbon particles, and metal sols, they can provide this function without modification. Where the particles are not opaque, they are usually rendered light absorptive by causing an appropriately absorbing dye to become bound or dissolved into the particle matrix. Alternatively, the particle can carry a chemical on its surface that serves to render the product non-fluorescent by chemical modification of the product. Also useful in the present invention are particles that can be moved away from the light path of the spectrometer to avoid detection of products that become bound to them. For this purpose it is desirable to use relatively large particles, usually 300 nm to 100 microns in diameter or to provide means to aggregate smaller particles to obtain aggregates of this size. Particularly preferred particles of this type are paramagnetic particles, frequently latex particles with a paramagnetic core or magnetite particles.

Binding of receptors, antibodies and other molecules to the particles may be accomplished by well-known techniques commonly available in the literature. See, for example, "Immobilized Enzymes," Ichiro Chibata, Halsted Press, New York (1978) and Cuatrecasas, *J. Biol. Chem.*, 245:3059 (1970).

Energy absorber or quencher—a diverse number of energy absorbers or quenchers may be employed in the present invention. The quencher must be able to quench the fluorescence of the fluorescer when brought into proximity with the fluorescer by virtue of the binding of the probes. Quenchers are chromophores having substantial absorption higher than 310 nm, normally higher than 350 nm, and preferably higher than about 400 nm. Preferably, the quenchers will absorb particularly strongly at the wavelength of emission of products produced from amines other than homocysteine with the first compound. Generally, the quencher lacks or has only weak fluorescence. For example, one group of quenchers is the xanthene dyes, which include the fluoresceins derived from 3,6-dihydroxy-o-phenylxanthhydrol and rhodamines, derived form 3,6-diamino-9-phenylxanthhydrol that have one or more substituents which render these dyes relatively non-fluorescent. Alkoxy groups in the 4 or 5 position of the xanthene and electron rich groups such as amines, hydroquinones, hydrazines and the like can be used.

Energy acceptors that are non-fluorescent can include any of a wide variety of azo dyes including, for example, α-naphthyl red, disperse orange, basic blue 66, oil red O and the like, 4,5-dimethoxyfluorescein, formazans, indophenols and the like.

Another example of quenchers that may be used is energy absorbent or quenching particles. Examples of such particles are carbon particles, such as charcoal, lampblack, graphite, colloidal carbon and the like. Besides carbon particles metal sols may also find use, particularly of the noble metals, gold, silver, and platinum. Other metal derived particles may include metal sulfides, such as lead, silver or copper sulfides or metal oxides, such as iron or copper oxide.

Heller (U.S. Pat. No. 5,565,322) discloses donor and acceptor chromophores at column 9, line 37, to column 14, line 7, the disclosure of which is incorporated herein by reference. A further discussion of fluorescers and quenchers may also be found in U.S. Pat. Nos. 4,261,968, 4,174,384, 4,199,983 and 3,996,345, the relevant disclosures of which are incorporated herein by reference.

Signal deactivator—a group, particle, or surface that serves to quench or remove the signal produced by a product of the first compound with a sample component. The group may directly quench the signal by virtue of it being an energy acceptor, quencher, opaque or colored particle and the like. Alternatively, the group may be comprised of a ligand or a chemically active moiety, such as a sulfhydryl group, which can react respectively with a receptor or chemically reactive partner such as an alkylating agent to quench or remove the signal produced by the product. Particles or other surfaces that become part of or can bind to the product can also serve as signal deactivators by virtue of their ability to absorb light or to facilitate physical separation of the product from the site that detection of the product takes place.

Support or surface—a porous or non-porous water insoluble material. The support can be hydrophilic or capable of being rendered hydrophilic and includes inorganic powders such as silica, magnesium sulfate, and alumina; natural polymeric materials, particularly cellulosic materials and materials derived from cellulose, such as fiber containing papers, e.g., filter paper, chromatographic paper, etc.; synthetic or modified naturally occurring polymers, such as nitrocellulose, cellulose acetate, poly (vinyl chloride), polyacrylamide, cross linked dextran, agarose, polyacrylate, polyethylene, polypropylene, poly(4-methylbutene), polystyrene, polymethacrylate, poly (ethylene terephthalate), nylon, poly(vinyl butyrate), etc.; either used by themselves or in conjunction with other materials; glass available as Bioglass, ceramics, metals, and the like. Natural or synthetic assemblies such as liposomes, phospholipid vesicles, and cells can also be employed.

Binding of sbp members to a support or surface may be accomplished by well-known techniques, commonly available in the literature. See, for example, "Immobilized Enzymes," Ichiro Chibata, Halsted Press, New York (1978) and Cuatrecasas, *J. Biol. Chem.*, 245:3059 (1970). The surface can have any one of a number of shapes, such as strip, rod, particle, including bead, and the like.

Mercaptan—means a thiol, i.e., a derivative of hydrogen sulfide in the same way that alcohols are derivatives of water. Mercaptans include those thiols having from one to 20 carbon atoms, either straight chain or branched, such as, for example, methanethiol, ethanethiol, propanethiol, butanethiol, 2-methylpropanethiol, pentanethiol, 2-methylbutanethiol, and so forth.

In one approach for the assay of Hcy, the sample suspected of containing Hcy is combined with a first compound, e.g., o-phthalaldehyde (OPA) in the absence of an added thiol and the product of Hcy and OPA is determined without separation of the product from the assay medium. The structure of the product of this reaction is as follows:

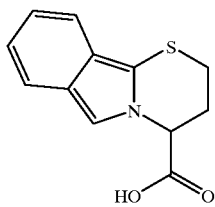

Hcy reacts more rapidly with OPA than Cys to form a cyclic product because the Hcy product lacks the strained 5-membered fused ring that is formed at elevated temperatures from Cys. The reaction can, therefore, be stopped prior to the formation of a significant amount of the Cys product. Even if the rates of formation of the products from Hcy and Cys were similar, the Cys product, as explained above, is weakly fluorescent whereas the Hcy product is highly fluorescent. Thus, the fluorescence of the assay mixture reflects the amount of iso-indole formed from Hcy and, thus, the amount of Hcy in the sample.

If fluorescent products that are produced from amines other than Hcy interfere in the above determination, their interference can be eliminated in a number of ways. Antibodies may be added that bind to the interfering products but not to the cyclic Hcy product. The antibodies can be used to physically remove the interfering products or quench their fluorescence either as a direct consequence of binding or because the antibodies are labeled with a quencher. Alternatively, a non-immunochemical reagent could be added that further discriminates between the iso-indole formed from Hcy and other iso-indoles that may be present. For example, a dienophile such as acetylenedicarboxylic acid can be added or present at the outset of the reaction to form fumarate adducts from the Hcy product, which will have quite different chromophoric properties from the products formed from Cys, and other amines, and may therefore be distinguished spectroscopically. Other highly reactive dienophiles can be substituted for acetylene dicarboxylic acid such as, for example, 1,3,4-triazoline-2,5-dione, diethyl azodicarboxylic acid, and other acetylenes substituted with electronegative groups such as, for example, sulfonic acid esters, trifluoromethyl and the like.

In another approach the assay is conducted by combining the sample with OPA and a mercaptan that comprises a quencher (or other signal deactivator). Only the product derived from Hcy is cyclic and unstrained and will, therefore, not have incorporated the mercaptan and quencher. By contrast the Cys product is either not formed because slow cyclization permits interception of an intermediate by the mercaptan or it is sufficiently unstable that it reacts with the mercaptan after it is formed. In either case quencher is incorporated into the product thus rendering it non-fluorescent. The isoindoles formed from other amines in the presence of the mercaptan will likewise contain the quencher and be non-fluorescent. Following addition of the OPA and mercaptan, the fluorescence of the mixture is measured without separation of the product from the assay mixture and the amount of fluorescence is related to the amount of Hcy product and, thus, the amount of Hcy in the sample.

Another embodiment is similar to the aforementioned approach except that the mercaptan comprises a ligand that need not be a quencher. The sample is first mixed with OPA or an analog thereof and the mercaptan. The isoindole products into which the mercaptan becomes incorporated are then physically removed or quenched by addition of a scavenger that reacts with the ligand. The signal not associated with the quencher or particles is measured to determine the amount of Hcy product and, thus, the amount of Hcy in the sample.

The scavenger can be a chemical substance that reacts with the ligand or a receptor for the ligand such as an antibody. Normally, the scavenger is attached to a quencher or a surface such as a particle surface that provides means for separating the captured ligand from the light path. When particles are used separation will usually be achieved by allowing the particles to settle or by moving them to one side of the reaction vessel by other means such as by use of a magnetic field. Thus, the reaction permits physical removal of the interfering products, quenching of their fluorescence, or deactivation of any other physical property to be employed for detection of the Hcy product in the assay. A particularly attractive scavenger comprises an alkylating agent that reacts rapidly with mercaptans such as a maleimide or α-haloamide in which case the ligand is a mercaptan; that is, the mercaptan used in the assay has two thiol groups, one of which enters into reaction with the OPA and the other of which serves as the ligand.

In another approach an OPA derivative is used to permit improved discrimination between Cys and Hcy. The OPA derivative is designed to cause a substantial difference in the fluorescent properties of the two products. For example, a naphthoquinone-5-carboxaldehyde can be substituted for OPA. The structures of the products of this reaction are respectively as follows:

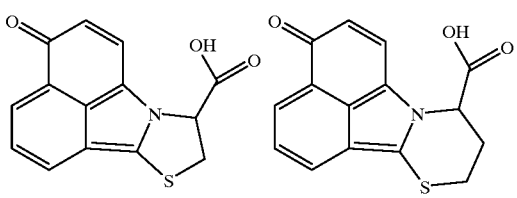

The products of reaction with Cys and Hcy are then 4-aza-1-acenaphthones having 5- or 6-membered rings fused to the acenaphthone 5-membered ring. The differences in the position of the carboxyl relative to the aromatic group in these products affects the fluorescence properties of these products. In one approach the 3- position of a naphthoquinone-5-carboxaldehyde is substituted by a group that can further react with the carboxyl group of the product such as, for example, a bromomethyl group. The product formed from Hcy, but not Cys, has its carboxyl group close to this group. Displacement of the bromine gives a cyclic lactone that has modified spectral properties rendering it readily distinguishable from other products that might be formed.

For point of care applications an assay method that permits detection of the product on a support is often desirable. A method similar to one described above can be used for this purpose. OPA and a mercaptan-labeled ligand such as 1-(biotinylamino)-2-ethanethiol are dried to a spot on a bibulous strip. Streptavidin is non-diffusively bound to a site upstream of this spot and antibodies to the iso-indole from Hcy are non-diffusively bound to a site further upstream. The sample is applied to the spot and allowed to wick along the bibulous strip. Only the cyclic iso-indole products are carried past the streptavidin and pass into the zone containing the antibody where they will be captured. The fluorescence intensity at the zone containing antibody then indicates the amount of Hcy in the sample.

As a matter of convenience, predetermined amounts of reagents employed in the present invention can be provided in a kit in packaged combination. A kit can comprise in packaged combination (a) a compound that comprises a cis-1,4-dioxo-2-butene moiety or hydrolytically derived precursor thereto and (b) other reagents for conducting a method for determining the amount of Hcy in a sample. Such reagents include those mentioned above such as, for example, a ligand comprising a mercaptan, a signal deactivator comprising a mercaptan including quenchers and particles, receptors for the ligand bound to a signal deactivator, receptors for a product formed from Hcy and the cis-1,4-dioxo-2-butene moiety or hydrolytically derived precursor thereto, reagents that react with the product formed from Hcy and the cis-1,4-dioxo-2-butene moiety or hydrolytically derived precursor thereto so as to enhance the signal or differentiate the signal from that produced by interfering substances in a sample, and the like.

The kit can further include various buffered media and solvents, some of which may contain one or more of the above reagents, bibulous strips carrying one or more of the reagents and cassettes or holders for the strips.

The relative amounts of the various reagents in the kits can be varied widely to provide for concentrations of the reagents necessary to achieve the objects of the present invention. Under appropriate circumstances one or more of the reagents in the kit can be provided as a dry powder, usually lyophilized, including excipients, which on dissolution will provide for a reagent solution having the appropriate concentrations for performing a method or assay in accordance with the present invention. Each reagent can be packaged in separate containers or some reagents can be combined in one container where cross-reactivity and shelf life permit. The kits may also include a written description of a method in accordance with the present invention as described above.

EXAMPLES

The invention is demonstrated further by the following illustrative examples. Parts and percentages are by weight unless otherwise indicated. Temperatures are in degrees Centigrade (° C.) unless otherwise specified. Unless indicated otherwise, chemicals were reagent grade and commercially available from sources such as Gibco (Rockville, Md.), Aldrich Chemical Company (Milwaukee, Wis.) and Sigma Chemical Company (St. Louis, Mo.). All solutions were prepared in water and all reactions were performed under ambient conditions unless otherwise stated. The following preparations and examples illustrate the invention but are not intended to limit its scope.

Example 1

Assay for Homocysteine or Cysteine

To 50 μL of 100 mM HEPES buffer, pH 7.3, containing l mM EDTA and 10 mM sodium cyanoborohydride was added 50 μL of a serum sample containing 10 to 50 μM homocysteine. The mixture was incubated for 5 minutes at 37° C. to reduce any disulfide bonds, and then combined with 100 μL of 4 mM naphthalene 2,3 dialdehyde in 20% aqueous methanol. The fluorescence of the resulting mixture was monitored by exciting with 510 nm light and detecting at the fluorescence signal maximum at 577 nm. The rate of appearance of fluorescence was monitored over 100 seconds and was proportional to the concentration of homocysteine. When the assay was repeated using cysteine instead of homocysteine, a very similar response was obtained except that the fluorescence emission maximum was at 566 nm. Other amino acids such as cysteine, which were present in the reaction mixture, did not give significant fluorescence under these conditions.

The above experiment is repeated with the exception that the naphthalene 2,3-dialdehyde is replaced by o-phthalaldehyde or 3-(2-furoyl)-quinoline-2-carboxaldehyde. The emission maxima for the products of the reaction of these aldehydes with homocysteine are respectively 490 and 520 nm and with cysteine they are 485 and 520 nm.

Example 2

Assay for Homocysteine

1. Preparation of antibodies to the fluorescent product of naphthalene 2,3-dialdehyde and cysteine. A 10% aqueous methanol solution of 5 mM cysteinylglycine (Sigma Chemical Company, St. Louis, Mo.) (5 ml) containing 100 mM HEPES (Life Technologies, Inc., Grand Island, N.Y.), pH 7.3, is added slowly with stirring to 1 ml of 4 mM naphthalene 2,3-dialdehyde (Aldrich Chemical Company, St. Louis, Mo.) in the same solvent over 60 minutes. After standing for an additional hour, the solution is evaporated to dryness and the residue is washed with sufficient amount of toluene (Aldrich) to remove excess naphthalene 2,3-dialdehyde. The washed residue is dissolved in 250 µL of dry dimethylformamide (Aldrich) containing 1 mg N-hydroxysuccinimide (Aldrich). 2.5 mg of 1-(3-dimethylaminopropyl)-3-ethylcarbodiimide (EDCl) (Aldrich) is then added and the mixture stirred overnight at 4° C. This solution is then added slowly to 1 ml of a solution of 2 mg bovine serum albumin (Sigma) in 55 mM Tris buffer (Tris HCl ×Tris(hydroxymethyl)aminomethane-HCl (a 10X solution) from BioWhittaker, Walkersville, Md.), pH 8.0, at 4° C. After two hours, the mixture is chromatographed over Sephadex G50 (Pharmacia, Piscataway, N.J.) by elution with distilled water and the albumin-containing fractions are evaporated to dryness. Balb/c mice are immunized with this immunogen using standard methods. After completion of the immunization schedule, the mice are sacrificed and spleenectomized and monoclonal antibodies are prepared according to standard procedures as described in U.S. Pat. No. 5,328,828, the relevant disclosure of which is incorporated herein by reference. Hybridoma clones are selected based on the ability of the culture supernates to quench the fluorescence of the cysteinenaphthaldehyde product without quenching the fluorescence of the corresponding homocysteine product. These clones are expanded and the antibodies isolated from the tissue culture media.

2. Specific assay for homocysteine. To 50 µL of 100 mM HEPES buffer, pH 7.3, containing 1 mM EDTA and 10 mM sodium cyanoborohydride (Aldrich) are added 50 µL of a solution containing 10 to 50 µM homocysteine (Aldrich) with and without added cysteine (Aldrich). The mixtures are incubated for 5 minutes at 37° C. and then combined with 100 µL of 4 mM naphthalene 1,2-dialdehyde (Aldrich) in 20% aqueous methanol. After an additional 15-minute incubation, 200 µg of an antibody prepared as described above in 25 µL of the above buffer is added. The fluorescence of the resulting mixture is monitored by exciting with light at 510 nm and detecting at the fluorescence signal maximum at 577 nm. The rate of appearance of fluorescence is monitored over 100 seconds and is proportional to the concentration of homocysteine and independent of the presence of cysteine. Other amino acids do not give significant fluorescence under these conditions.

Example 3

1. Preparation of immunogen

Cystine bis-o-nitrobenzyl ester

Into a 250 µL round bottom flask equipped with a magnetic stirring bar was added 1.2 g (5.0 mmole) of cystine, 3.8 g (25 mmol) of o-nitrobenzyl alcohol, and 3.0 g (5.0 mmole) of p-toluenesulfonic acid in 150 mL of dry acetonitile. The solution was stirred at reflux for 6 hours with azeotropic removal of water and the solvent then removed on a rotary evaporator at room temperature under vacuum. The residue was partitioned between ethyl acetate and aqueous base, pH 11, and the aqueous layer washed four times with the same solvent and three times with methylene chloride. The combined organic layers were washed with water, pH 8, dried over sodium sulfate, filtered and concentrated under reduced pressure. The residual brown oil was purified by column chromatography on silica gel. 1H NMR (CDCl$_3$) d 1.85 (broad m, 4H, CH$_2$S), 3.75 (m, 2H, CHCO), 5.40 (S, 4H, OCH$_2$Ar), 7.4–8.1 (m, 8H, ArH)

Cysteine o-nitrobenzyl ester

Cystine bis-o-nitrobenzyl ester was taken up in methanol containing an equimolar concentration of NaBH$_4$ and the mixture allowed to stand at room temperature for 10–15 minutes. The reaction was followed by TLC on silica using 10:3 ethyl acetate:methanol, starting material Rf=0.65, product Rf=0.71.

3-(p-carboxybenzoyl)quinoline-2-carboxaldehyde (CBOCA) adduct of cysteine o-nitrobenzyl ester A solution of 4.2 mL of methanol and 2.2 mL of HEPES buffer, pH 5.5, containing 10 mg (0.033 mmol) of CBQCA was degassed and combined with the above reaction mixture containing 8.5 mg (0.04 mmol) of cysteine o-nitrobenzyl ester. The solution became dark brown and was stirred at room temperature for 4–5 hours and then at 4° C. overnight. The reaction was followed by TLC on silica using 7:3 methanol:ethyl acetate, CBQCA Rf=0.87, product Rf=0.24. Following disappearance of the CBQCA spot the methanol was evaporated by blowing with a stream of argon. The precipitated product was purified by preparative TLC. 1H NMR (CD$_3$OD): d 2.42 (broad t, 2H, CH$_2$S), 3.4 (dd, 1H, CHCO), 5.2 (s, 2H, OCH$_2$), 7.5–8.5 (broad m, 13H). Dissolution of an aliquot of the sample in methanol followed by irradiation with a 150 watt tungsten-halogen lamp produced a fluorescent solution with an emission maximum at 544 nm BSA conjugate of the CBOCA adduct of cysteine (CBOCA-Cys-BSA immunogen)

A 1 mL dimethylformamide solution containing 17 mg (0.033 mmol) of the CBQCA adduct of cysteine o-nitrobenzyl ester, 9.5 mg (0.05 mmole) of 1-ethyl-3-(3-dimethylaminopropyl)-carbodiimide hydrochloride (EDAC), and 8.0 mg (0.07 mmol) of N-hydroxysuccinimide was stirred at room temperature for 3 hours. The solution of the resulting N-hydoxysuccinimide ester was added to 2 mL of 0.1 mM phosphate buffer (pH 7.2) containing 60 mg BSA and 0.1 mM EDTA, and the mixture was agitated at room temperature for 3 hr. The product was isolated on a PD-10 Sephadex G-25M column using a phosphate buffer. The fractions were irradiated using a 150 watt tungsten-halogen lamp until there was no further increase in fluorescence. The most strongly fluorescent fractions were pooled and lyophilized to yield a light yellow solid. A solution in HEPES buffer, pH 7.3, showed a fluorescence emission maximum at 544 nm. Approximately 55% of the amines of the protein had reacted with the active ester as shown by titration of residual amines with tetranitrobenzene sulfonic acid.

CBOCA adduct of cysteine (CBOCA-Cys)

Cysteine (17 mg, 0.14 mmol) in 3 mL HEPES buffer, pH 7.3, was added to a solution of 30 mg (0.1 mmol) CBQCA in 5 mL methanol. The reaction was monitored by TLC on silica using 7:3 ethanol:ethyl acetate, CBQCA Rf=0.87, yellow fluorescent product Rf=0.4. After stirring for 1 hour at room temperature and standing overnight at 4° C. the solvent was removed in vacuo and the residue used in the next step without further purification.

CBOCA adduct of cysteine-biotin conjugate (CBOCA-Cys-biotin)

A solution of 39 mg of the above residue, 20 mg of dicyclohexylcarbodiimide, and 20 mg of N-hydroxysuccinimide in 5 mL of dry dimethylformamide was stirred at room temperature overnight. To the resulting suspension was added 32.4 mg (1.1 equivalents) of N-(5-aminopentyl)-biotinamide in 2 mL dimethylformamide and stirring was continued for 20 hours at the same temperature. The product was isolated by filtration and washing of the precipitate with methylene chloride. The combined solutions yielded a crystalline product, which was further purified by preparative TLC. The NMR was consistent with one of the two possible biotinyl amides: 1H NMR (DMSO) d: 1.13–1.56 (m, 12H, 6CH$_2$), 2.01 (t, 2H, CH$_2$CON), 2.35 (t, 2H, CH$_2$S+1H, CH$_2$SC=), 3.00 (m, 1H, CHS+1H, CH$_2$SC=), 3.29 (broad s, 4H, CH$_2$NH), 3.46 (t, 1H, NCHCO), 4.1 (m, 1H, CH—NH), 4.29 (m, 1H, CH—NH), 7.68–8.20 (m, 9H, ArH)

Naphthalene-2,3-dicarboxaldehyde adduct of cysteine (Nap-cysteine)

A solution of cysteine (9.2 mg, 0.075 mmol) in 1 mL HEPES buffer, pH 7.3, containing 100 mM of EDTA was purged of oxygen by bubbling with argon and added to a solution of 70 mg (0.38 mmol) of naphthalene-2,3-dicarboxaldehyde in 7 mL methanol and 3 mL of the same buffer that had been similarly purged. The product precipitated following stirring for 30 minutes and blowing with a stream of argon to evaporate the methanol and was further purified by TLC using 11% methanol in methylene chloride. 1H NMR (CD$_3$OD): d 3.45 (m, 2H, CH$_2$S), 3.94 (dd, 1H, NCHCO), 7.58–8.43 (m, 7H, ArH). Fluorescence: EX-490 nm, EM-534 nm.

Naphthalene-2,3-dicarboxaldehyde adduct of homocysteine (Nap-homocysteine)

A solution of cysteine (7.4 mg, 0.05 mmol) in 1 mL HEPES buffer, pH 7.3, containing 100 mM of EDTA was purged of oxygen by bubbling with argon and added to a solution of 50 mg (0.27 mmol) of naphthalene-2,3-dicarboxaldehyde in 5 mL methanol and 4 mL of the same buffer that had been similarly purged. The product precipitated as a yellow solid following stirring for 30 minutes and blowing with a stream of argon to evaporate the methanol. It was dried and further purified by TLC using 25% methanol in methylene chloride. 1H NMR (CDCl$_3$): d 0.85 (q, 2H, CH$_2$), 2.42 (t, 2H, CH$_2$S), 3.48 (dd, 1H, NCHCO), 7.47–8.82 (m, 7H, ArH). Fluorescence: EX-490 nm, EM-536 nm.

2. Preparation of antibodies to Nap-cysteine Immunizations

The CBQCA-Cys-BSA immunogen was prepared as described above. BALB/c mice were immunized subcutaneously with 100 mg in Complete Freunds' Adjuvant. Additional booster injections of 50 mg were given after 2, 5, 7, 9 13 and 17 weeks. 500 mg injections of the immunogen in PBS were subsequently given on days 177, 178, and 179. Blood was collected at various intervals during this period up to day 181. On day 181 the mice were sacrificed and the splenocytes fused. The plasma was stored at −20° C. and diluted before analysis in Dulbecco's PBS (calcium and magnesium free) containing non-fat dry milk proteins.

Tissue Culture

S-DMEM was used for all tissue culture, which consisted of Iscove's Modified Eagles Medium (DMEM) supplemented with 10% Fetal Bovine Serum (FBS)

Conditioned media was prepared by growing P388D1 cells (ATCC TIB 63) in S-DMEM and splitting 1:4 every four to five days. Spent media was centrifuged at 1500 rpm for 15 minutes. The spent media was then filtered using a 0.2 micron sterile tissue culture filter unit to remove any remaining cells and debris. Glutamine (100×stock=58.5 mg/L) was added to the spent media before using or freezing at −20° C. for future use. Conditioned S-DMEM, used to support hybridoma growth after fusion and during cloning, was prepared by supplementing S-DMEM with 10% spent media.

Fusions

Fusions were carried out essentially according to the procedure of Milstein and Kohler, Nature 256:495–497 (1975). Spleens were aseptically removed from immunized mice and placed in a 60 mm tissue culture dish containing 10 mL DMEM. They were minced a few times and then mashed between the ends of two frosted slides. A single cell suspension of splenocytes was attained by passing the cell suspension through a monofilament screen cloth. The splenocytes, about 2×10$^8$ cells, were combined with 40×10$^6$ Ag8.653 cells (a nonsecretor myeloma cell line from ATCC), centrifuged at 800 rpm for 5 minutes, and washed 1 to 2 times with DMEM. Fusion was performed by addition of 4.0 mL polyethyleneglycol (PEG) (50% solution in 75 mM HEPES), which was added over 3 minutes while gently stirring, and then 30 to 40 mL S-DMEM was added to inactivate the PEG. The cell suspension was centrifuged at 800 rpm for 5 minutes. The supernatant was poured off, and the cells were resuspended with 240 mL S-DMEM-HAT (100 mM hypoxanthine, 0.4 mM aminopterin, and 16 mM thymidine) and plated at 200 mL/well into twelve 96-well culture plates. Cells were fed by removal of 100 mL/well of spent media and subsequent addition of 200 mL/well of conditioned S-DMEM-HAT 4 to 5 days after the fusion. Fusions were screened about 7 to 10 days after the fusion. Hybridoma colonies were usually then visible by eye while the media was still pink or just turning yellow.

Cloning by Serial Dilution

Hybridomas producing ELISA positive antibodies were cloned several times by serial dilution to ensure single cell colonies. Contents from a well of a 96-well plate were transferred to a well in a 24-well plate containing 1.5 mL/well of conditioned S-DMEM. Cells were mixed by pipetting, and 100 mL/well were added to the first row of a 96-well plate containing 200 mL/well conditioned S-DMEM. One hundred mL/well were transferred to the second row using a Flow Multichannel pipettor, mixed by pipetting, and again 100 mL/well were transferred to the next row. Each "clone" was serially diluted 7 times, 1 to 4 clones per plate. Cells were recloned by limiting dilution 3 to 4 times or until stable.

Freezing and Thawing Cell Lines

Cloned and stabilized cell lines that were positive by ELISA (ELISA+) were stored at −100° C. The chosen well (clone) from a 96-well plate was grown up by daily passaging of cells and sequentially expanding from a 24-well plate with 1.5 mL/well S-DMEM, next into a 6-well plate with 8 mL/well S-DMEM, and finally into a T-75 flask with 50 mL S-DMEM. Cells from a T-75 flask were centrifuged at 800 rpm for 5 minutes and resuspended in 3 mL of freezing medium, 10% dimethylsulfoxide (DMSO) and 20% fetal bovine serum (FBS) in DMEM. One-mL (3–5×10$^6$ cells) aliquots were pipetted into cryovials, which were then placed in a freezing container. The container was then stored at −100° C. for 1–2 days, and then the vials were transferred to a −100° C. freezer storage box for later use. Cells were thawed by warming the vials in a 37° C. water bath. The cell suspension was transferred to a 15-mL centrifuge tube containing 5 mL of S-DMEM and then centrifuged at 800 rpm for 5 minutes. The supernatant was decanted and the cells resuspended in 8 mL of S-DMEM and pipetted into a 6-well plate for cell expansion.

Screening

Plasma samples and hybridomas were screened by ELISA using CBQCA-Cys-biotin (13):

A. Plates were coated by incubation with a 10 mg/mL solution of Fc specific goat anti-mouse antibody in PBS overnight at 4° C.

B. The plates were blocked by incubation with a solution of 10 mg/ml of non-fat dry milk proteins in PBS/0.05% sodium azide for at least 1 hour at room temperature and washed 4 times with PBS.

C. Hybridoma culture supernatant solutions or mouse sera diluted 500-fold in PBS were allowed to incubate in the wells for 1.5 hours and the wells then washed 4 times with wash buffer.

D. A solution of 3 mg/ml of CBQCA-Cys-biotin in S-DMEM was incubated in the wells for 1.5 hours at room temperature and the wells then washed 4 times with wash buffer.

E. A solution of horse radish peroxidase (HRP)-streptavidin conjugate (Zymed 43–4223, Zymed, South San Francisco, Calif.) diluted 1:3000 in incubation buffer (1 mg/ml BSA in PBS) was incubated in the wells for 1 hour at room temperature and the wells then washed 4 times with wash buffer.

F. A o-phenylenediamine (OPD) substrate solution (SigmaFast P-9187) was allowed to incubate in each well for 30 minutes in the dark.

G. The absorption of the solution in each well was measured at 450 nm and a reference reading was taken at 600 nm.

Antibodies were selected that produced an absorbance of at least 0.66 with 1.1 mg/ml of CBQCA-Cys-biotin using this protocol. Addition of 0.50 mg/ml of Nap-cysteine but not Nap-homocysteine suppressed the assay response to near the background absorbance of 2.2

Purification of antibodies

Antibody solutions are loaded onto a column containing Protein G that had been thoroughly washed with PBS pH 7.0 (0.01M sodium phosphate, 0.15M sodium chloride, 0.02% sodium azide). The column is washed with PBS until the optical density of the washings returned to baseline. Antibody is eluted with 0.5M acetic acid adjusted to pH 3.0 with ammonium hydroxide. The antibody peak is pooled and the solution dialyzed overnight against PBS, pH 7.4.

Conjugation of antibodies with a quencher dye

To a stirred 0.1 mmol dimethyl formamide (DMF) (2 ml) solution of 5,5'-dicarboxyindigo, prepared as described in U.S. Pat. No. 4,992,556, is dissolved N-hydroxysuccinimide (11.7 mg, 0.11 mmol). The mixture is then cooled in an ice bath and dicyclohexyl carbodiimide (DCC) (20.6 mg, 0.11 mmol) is added. The mixture is stirred overnight in a cold room (+5° C.). The reaction mixture is then filtered and 100 mL of this solution is added slowly using a syringe pump to a 1 ml solution containing 1 mg of antibody purified as above and adjusted to pH 8.5. The mixture is stirred in the cold room overnight and then concentrated to half its volume (Amicon filter, PM 30,000, Amicon Corporation). The conjugate is purified on a Sephadex G-50 column using PBS, pH 7.4, as eluting solvent. The protein fraction should have an average of over 15 dyes per antibody as determined by its absorption spectrum.

3. Assay for homocysteine

Anti-Nap-cysteine antibodies are selected that quench the fluorescence of Nap-cysteine for use in the assay. Antibody conjugated with 5,5'-dicarboxyindigo is preferentially used because conjugation provides increased quenching efficiency and leads to better specificity for homocysteine relative to cysteine. Aliquots (400 ml) of a 1.2 mM solution of 2,3-naphthalene dialdehyde in 120 mM HEPES buffer (0.12 mM ethylenediaminetetraacetate (EDTA), pH 7.3) containing 12% methanol are combined either with 75 ml of a solution of containing 1 mg/ml of non-specific mouse IgG or mouse anti-Nap-cysteine antibody in PBS, pH 7.4. To these solutions are added 25 ml of freshly prepared human serum supplemented with increasing amounts of homocysteine or cysteine. The fluorescence spectrum of each solution is measured immediately after mixing and at several times over a 90 minute incubation period by irradiation at 510 nm and reading of emission at 570 nm. The fluorescence increases nearly linearly on increasing the concentration of homocysteine or cysteine. The minimum detectable concentration of both cysteine and homocysteine in serum is about 100 nM when non-specific mouse IgG was used. When the anti-Nap-cysteine antibody is included in the solutions similar increases in the fluorescence are observed with added homocysteine but no increase is observed with added cysteine.

All publications and patent applications cited in this specification are herein incorporated by reference as if each individual publication or patent application were specifically and individually indicated to be incorporated by reference. A portion of the present disclosure contains material that may be subject to copyright protection. The copyright owner has no objection to the facsimile reproduction by anyone of the patent document or the patent disclosure as it appears in the U.S. Patent and Trademark Office patent files or records, but otherwise reserves all copyright rights whatsoever.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A non-immunochemical method for determining homocysteine in a liquid medium containing amines other than homoysteine, said method comprising:

(a) providing in combination in said medium the sample and a first compound that comprises a cis-1,4-dioxo-2-butene moiety or hydrolytically derived precursor thereto, (b) subjecting said combination to conditions under which homocysteine reacts with said cis-1,4-dioxo-2-butene moiety or hydrolytically derived precursor thereto to form a product, and (c) detecting said product without separation of said product from said medium.

2. The method of claim 1 wherein said product is a pyrrole.

3. The method of claim 1 wherein said first compound has the structure:

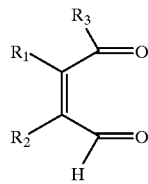

wherein $R^1$, $R^2$ and $R^3$ are independently hydrogen, alkyl, aryl, aralkyl, or alkylene, wherein one or more hydrogens of the above may each be substituted with a substituent and wherein $R^1$ and $R^3$ and/or $R^2$ may be taken together to form a 5 to 7 member ring, which contains one or more double bonds.

4. The method of claim 3 wherein said first compound is o-phthalaldehyde or naphthaquinone-5-carboxaldehyde.

5. The method of claim 1 wherein said combination further comprises a conjugate of a mercaptan and a second compound.

6. The method of claim 5 wherein said second compound is a signal deactivator.

7. The method of claim 6 wherein said signal deactivator is a ligand.

8. The method of claim 7 wherein products formed from said ligand in said method are removed from said medium prior to said detecting of said product.

9. The method of claim 7 further comprising adding to said medium a compound that reacts with said ligand.

10. The method of claim 7 wherein said ligand has a molecular weight of 100 to 2000 daltons.

11. The method of claim 7 wherein said ligand is a conjugate of a mercaptan and biotin.

12. A method for determining the amount of homocysteine in a sample, said method comprising:
(a) providing in combination said sample with one or more reagents that cause the formation of a product, said product having a six-membered ring fused to an unsaturated five-membered ring wherein the junction of said rings is comprised of the nitrogen of homocysteine and an atom that comprises a double bond, and wherein said six-membered ring comprises the sulfur atom of homocysteine,
(b) subjecting said combination to conditions under which homocysteine in said sample reacts with said one or more reagents to form said product, said product having a signal that is distinguishable from a signal corresponding to a product, if any, that is produced with cysteine, and
(c) detecting the amount of said product.

13. The method of claim 12 wherein said sample also contains amines other than homocysteine.

14. The method of claim 12 wherein said combination further comprises a conjugate of a mercaptan and a signal deactivator.

15. A method for determining homocysteine in a sample that also contains other amines, said method comprising:
(a) combining said sample with a first compound that comprises a cis-1,4-dioxo-2-butene moiety or hydrolytically derived precursor thereto in the presence of a reagent comprised of a sulfhydryl group and a signal deactivator,
(b) a scavenger for inhibiting signal from reaction products that contain the signal deactivator, and
(c) measuring the amount of signal from any reaction product that does not contain said signal deactivator as a measure of the amount of homocysteine in the sample.

16. A kit for use in a method for determining homocysteine in a sample, said kit comprising in packaged combination:
(a) a first compound that comprises a cis-1,4-dioxo-2-butene moiety or hydrolytically derived precursor thereto and
(b) at least one reagent selected from the group consisting of dienophiles, mercaptans comprising a signal deactivator, ligands comprising a mercaptan and a scavenger that reacts with the ligand, signal deactivators comprising a mercaptan. receptors for the ligand bound to a signal deactivator, receptors for a product formed from homocysteine and the cis-1,4-dioxo-2-butene moiety or hydrolytically derived precursor thereto, and reagents that react with the product formed from homocysteine and the cis-1,4-dioxo-2-butene moiety or hydrolytically derived precursor thereto so as to enhance the signal or differentiate the signal from that produced by interfering substances in a sample.

17. The kit of claim 16 wherein said first compound is o-phthalaldehyde or naphthaquinone-5-carboxaldehyde.

18. The kit of claim 16 wherein said signal deactivator is a ligand.

19. The kit of claim 18 wherein said ligand has a molecular weight of 100 to 2000 daltons.

20. The kit of claim 18 wherein said ligand is biotin.

* * * * *